United States Patent [19]

Yamamoto et al.

[11] 4,410,277

[45] Oct. 18, 1983

[54] APPARATUS FOR DETECTING MAGNETO-OPTICAL ANISOTROPY

[75] Inventors: Manabu Yamamoto, Odawara; Masahiro Ojima, Kokubunji, both of Japan

[73] Assignee: Hitachi, Ltd., Tokyo, Japan

[21] Appl. No.: 201,483

[22] PCT Filed: Oct. 26, 1979

[86] PCT No.: PCT/JP79/00272

§ 371 Date: Jun. 30, 1980

§ 102(e) Date: Jun. 30, 1980

[87] PCT Pub. No.: WO80/01016

PCT Pub. Date: May 15, 1980

[30] Foreign Application Priority Data

Nov. 1, 1978 [JP] Japan ......................... 53/149556[U]

[51] Int. Cl.$^3$ .......................... G01N 21/21; G01J 4/04
[52] U.S. Cl. ..................................... 356/366; 356/367; 356/369; 360/114; 365/122
[58] Field of Search ................. 356/365–369, 356/364, 370; 365/122; 350/377; 360/114

[56] References Cited

U.S. PATENT DOCUMENTS

| | | | |
|---|---|---|---|
| 3,445,833 | 5/1969 | Lins | 356/368 |
| 3,775,570 | 11/1973 | Lewicki et al. | 365/122 |
| 4,105,338 | 8/1978 | Kuroha | 356/369 |

OTHER PUBLICATIONS

Aben et al., "Photoelectric Magnetopolarimeter for Studying Inhomogeneous Optically Anisotropic Media", Sov. J. Opt. Technology 9–1977, pp. 534–536.
Matsuura et al., "Measurement of Flow–Birefringence Using a Circularly Polarized Laser Beam", Optics & Laser Tech. 10–1978, pp. 237–240.
Treves, D. "Magneto–Optic Detection of High Density Recordings", Jr. App. Physics 3–1967, pp. 1192–1196.
Lentz et al., "Magneto–Optical Readout" Electronics 9–1–61, pp. 36–39.

Primary Examiner—William H. Punter
Attorney, Agent, or Firm—Antonelli, Terry & Wands

[57] ABSTRACT

This invention relates to an apparatus for detecting magneto-optical anisotropy which can be utilized as an information reproduction apparatus for detecting information recorded on a magnetic medium. The apparatus consists of a light source (10), a magneto-optically anisotropic medium (20), a polarization analyzer (33A) and a light detector (34). To avoid the information reproduction by means of the linearly polarized light as in the prior art, the apparatus of the present invention reproduces the information using the light source (10) which generates the elliptically polarized light. This makes it possible to reproduce the information having a high signal-to-noise ratio.

1 Claim, 20 Drawing Figures

APPARATUS FOR DETECTING MAGNETO-OPTICAL ANISOTROPY

TECHNICAL FIELD

This invention relates to an apparatus for detecting magneto-optical anisotropy of a magnetic medium. The magneto-optical anisotropy dealt with in this invention represents the property such as double refraction and circular dichroism, that changes the linearly polarized light into the elliptically polarized light or causes a change in the ellipticity of the elliptically polarized light. The term "elliptically polarized light" used in this specification includes the circularly polarized light as a special case where the ellipticity takes a specific value.

BACKGROUND ART

In an apparatus used conventionally, as a magneto-optical anistropy detector of a magnetic medium, for reading out information recorded in accordance with the magnetized state of the magnetic medium, when the linearly polarized light passes through the magnetic medium or is reflected on the surface of the magnetic medium, the incident linearly polarized light is slightly converted into the elliptically polarized light and the principal axis of the ellipse slightly rotates from the polarizing direction of the incident linearly polarized light. Conventionally, the rotational angle of the principal axis of polarization is measured using a polarizing element and a polarization analyzer, but this method involves the drawbacks in that the apparatus is complicated and a signal-to-noise ratio is low.

DISCLOSURE OF INVENTION

The present invention provides an apparatus for detecting magneto-optical anisotropy which employs the elliptically polarized light in order to eliminate the abovementioned problems with the conventional magneto-optical anisotropy detector and which has a wider range of application and higher performance by measuring the change of the ellipticity of the elliptically polarized light.

BEST MODE FOR CARRYING OUT THE INVENTION

Hereinafter, the present invention will be explained in detail with reference to embodiments thereof.

Figure 1:
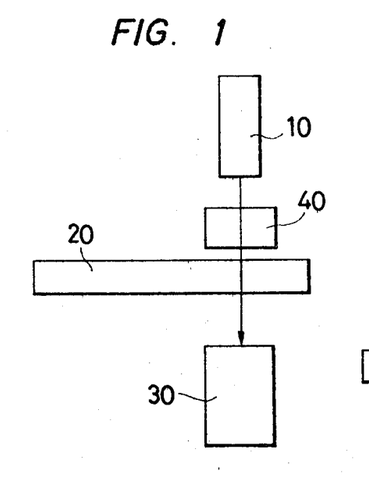
FIGS. 1 and 2 are block diagrams useful for explaining the fundamental construction of the present invention.
Figure 2:
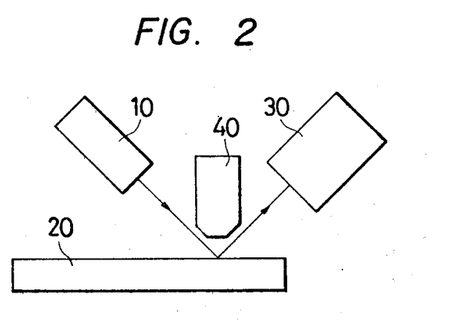

FIGS. 1 and 2 illustrate the fundamental construction of the present invention. More specifically, FIG. 1 shows the apparatus of a transmission type in which the ray of light passes through a medium and FIG. 2 shows the apparatus of a reflection type in which the ray of light is reflected by the medium. In both drawings, the same reference symbols represent the same parts or the same constituent members.

In FIGS. 1 and 2, reference numeral 10 represents a light source for the circularly polarized light or for the elliptically polarized light; 20 is a magneto-optically anisotropic medium; 30 is a polarization analysis means; and 40 is optical anisotropy-inducing means. If the magneto-optically anisotropic medium 20 is a substance having by itself natural anisotropy due to its magnetic structure or the like and if it is desired to observe such a substance, the optical anisotropy-inducing means as the additional means are not always necessary.

In most cases, the magnetizing direction of the magneto-optically anistropic medium 20 is parallel or perpendicular to the surface of the medium. However, the present invention can be applied even when the magnetizing direction is an optional direction other than the abovementioned directions.

Figure 3:
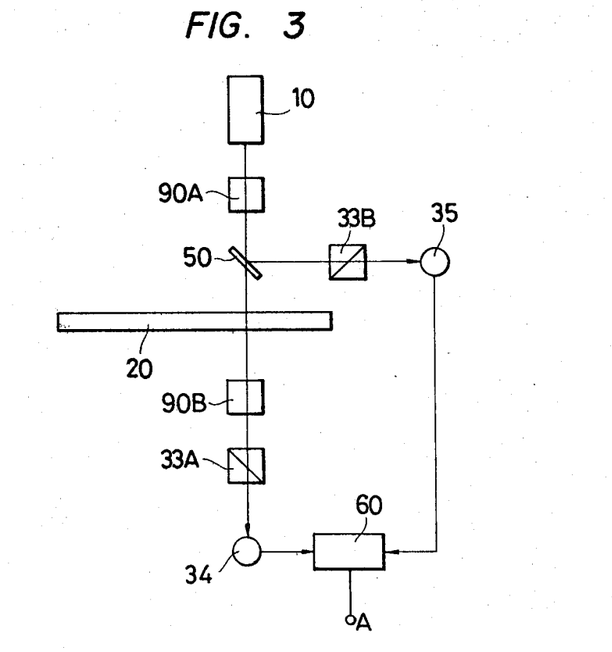
FIG. 3 is a block diagram showing the construction of an embodiment of the apparatus for detecting the magneto-optical anisotropy of the present invention.

An embodiment of the apparatus in accordance with the present invention is shown in FIG. 3. In this drawing, the ray of light of the light source 10 emitting the elliptically polarized light is incident to the magneto-optically anisotropic medium 20 and its transmission light is detected by a light receiver 34 via a polarization analyzer 33A. The magnitude of the optical anisotropy of the medium 20 appears as a change of the quantity of light received by the light receiver 34. This change of the quantity of the light can be detected further accurately by employing a differential means, or a means comprising detecting a part of the ray of light of the light source 10 by means of a beam splitter 50, a polarization analyzer 33B and a light receiver 35, comparing the quantity of the light detected thereby with that of the light receiver 34 using a comparator 60 and producing the output at an output terminal A.

The characterizing feature of the present invention lies in that a light source for the elliptically polarized light of which ellipticity is not zero, that is, a light source not for the linearly polarized light, is employed as the light source. Even when the light source for the linearly polarized light is employed as the light source, however, the similar object can be accomplished by adding means for generating the elliptically polarized light consisting of a phase plate or a double refraction element, a circular dichroism element and the like to the optical path in addition to the abovementioned constituent elements.

The inserting position of the phase plate or the circular dichroism element in the latter case is between the light source 10 and the medium 20 as represented by 90A or between the medium 20 and the polarization analyzer 33A as represented by 90B in FIG. 3.

Figure 4:
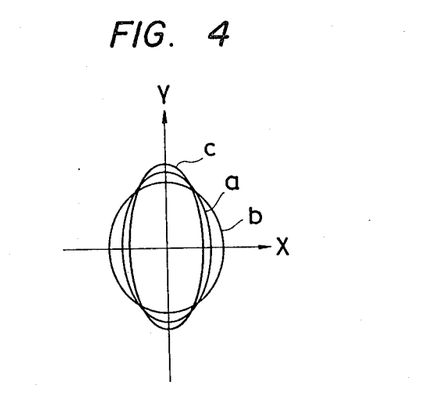
FIG. 4 is a schematic view of the polarized state of light useful for explaining the operation of the embodiment shown in FIG. 3.

Owing to the abovementioned construction, the apparatus of the present invention is characterized in that the apparatus makes it possible to detect not only the magnitude but also the polarity of the magneto-optical anisotropy of the magnetic medium with a high level of sensitivity. As a definite example, it will now be assumed that the medium 20 is one that exhibits magneto-optical circular dichroism such as a thermo-magnetic recording medium, and that the magnetizing direction is parallel to the optical path. If this medium is not present, the ray of light incident to the polarization analyzer 33A is elliptically polarized light of a certain ellipticity as represented by an ellipse a in FIG. 4. In FIG. 4, however, the ordinate Y and the abscissa X represent the amplitude of the light in the electric field in two directions crossing at a right angle with each other. Owing to the presence of the medium 20, change occurs in the ellipticity so that the ray of light becomes elliptically polarized light as represented by an ellipse b of FIG. 4, for example. Accordingly, if the polarizing direction of the polarization analyzer is the direction of the X axis, this change in the ellipticity depends upon the magnitude of magnetization. If magnetization of the medium 20 inverses, the elliptically polarized light changes into the shape such as shown by an ellipse c in the drawing. When compared with the original elliptically polarized light a, the intensity of the light in the direction of the X axis is decreased. In this manner, it becomes possible to simultaneously detect the magnitude and polarity of the magnetic circular dichroism by means of the change of the ellipticity.

What is of importance in the abovementioned embodiment is that the ellipticity of the elliptically polarized light incident to the medium must be set to a value greater than a certain value. Otherwise, the minimum state of the ellipticity represented by the ellipse c of FIG. 4 becomes extremely approximate to the linearly polarized light and the polarization component in the direction of the X axis becomes extremely small. Under such a state, the signal output is small and is susceptible to noise disturbance due to incompleteness of the light detecting element or to the dark current of the light receiver. The signal output, or the change quantity of the ellipticity, increases with the ellipticity in such a range where the ellipticity of the incident elliptically polarized light is not very great. Irrespective of the magnetization state of the magnetic medium, therefore, the ellipticity of the incident elliptically polarized light must be set so that the elliptically polarized light is constantly incident to the polarization analyzer. This can be accomplished by sufficiently inclining the principal axis of the aforementioned phase plate relative to the polarizing direction of the incident light to the phase plate. In the case of the abovementioned circular dichroism element, the arrangement must be made so that the difference of the adsorption factors to the right and left circularly polarized light becomes sufficiently large.

When setting is made in the abovementioned manner, a signal-to-noise ratio can be improved drastically.

So long as the ellipticity is not extremely small, the rotation of the principal axis of the ellipse due to the magneto-optical effect can be neglected.

Figure 5:
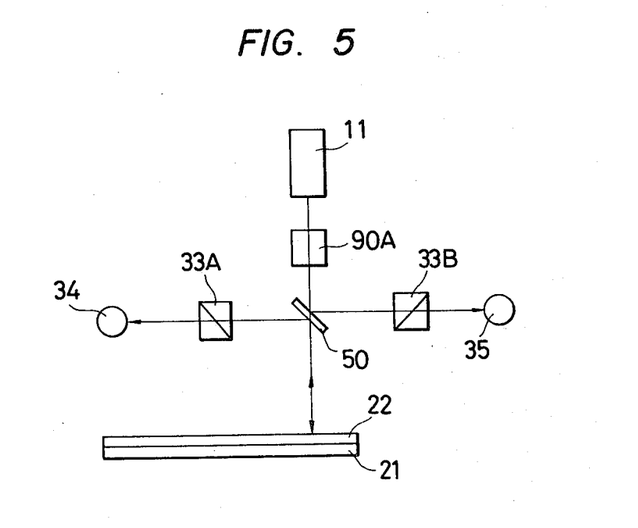
FIG. 5 is a block diagram showing the construction when the present invention is applied to a magnetic disc.

If, in FIG. 3, the medium 20 is constructed by a magnetic thin film formed on a substrate so as to represent information by means of the intensity of magnetization or its polarity, it can be utilized as an information recording medium corresponding to a so-called magnetic disc. FIG. 5 shows its embodiment. The optically anisotropic medium is constructed by forming the magnetic thin film 22 on the substrate 21. The ray of light of the light source for the linearly polarized laser is converted into elliptically polarized light or circularly polarized light by a double refraction element 90A, passes through a beam splitter 50, is reflected by the magnetic, optically anisotropic medium and is detected by the receiver 34 via the beam splitter 50 and the polarization analyzer 33A. The ray of light reflected by the medium 20 is changed into the elliptically polarized light of the ellipticity varying from that of the incident light due to the magnetic Kerr effect. This change is detected by the abovementioned method.

Figure 6:
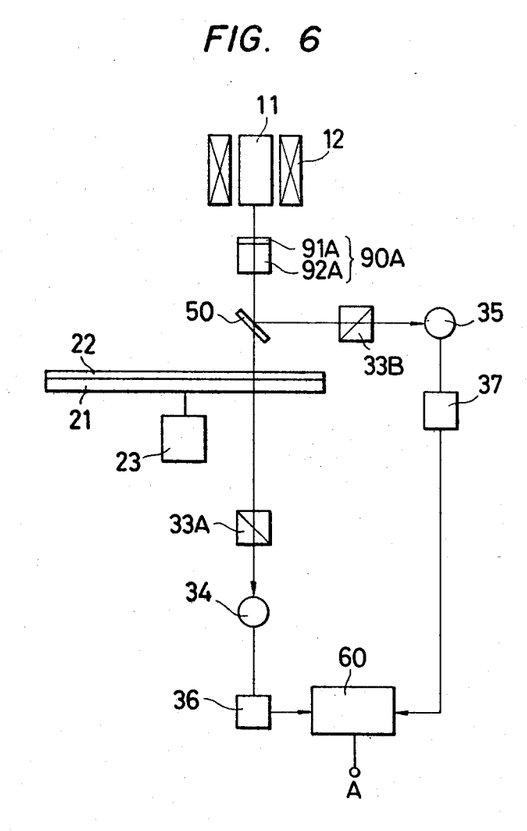
FIG. 6 is a block diagram showing the construction of another embodiment of the apparatus for detecting the magneto-optical anisotropy of the present invention.

FIG. 6 shows another embodiment of the present invention. The light source is a Zeeman laser. The Zeeman laser has a laser 11 and a magnetic field generation apparatus 12 and generates right circularly polarized right and left circularly polarized light having a different frequency from each other. This relies upon the Zeeman effect and is a known technique. According to the heretofore known Zeeman laser technique, a resonator length is automatically adjusted so that the intensity of the right and left circularly polarized light becomes equal to each other. According to this arrangement, a composite wave of the right and left circularly polarized light is linearly polarized light and the polarizing direction of the linearly polarized light rotates with the time. This linearly polarized light is converted into the elliptically polarized light by means of an elliptically polarized light generator 90A. This generator is produced by forming a magnetic, circular dichroic thin film 91A on a substrate 92A, for example. The optically anisotropic medium is produced by forming a thin layer 22 of a thermomagnetic recording substance on a substrate 21 and is actuated for rotation by a motor 23.

The characterizing feature of the apparatus of this embodiment resides in that since the ray of light generated from the Zeeman laser consists of plural oscillation lines having varying frequencies from one another, they generate beat due to their mutual interference so that the ray of light incident to the light receivers 34 and 35 is subjected to the intensity-modulation. In view of this fact, in the embodiment shown in FIG. 6, band-pass filters 36 and 37 are added behind the light receivers 34, 35. The center frequency of the band-pass filters is tuned with the abovementioned modulation frequency and their frequency is set so as to be higher than the frequency of the signal generated from the recording medium 20. The band width of the filter is set so as to be equal to, or higher than, the band width of the abovementioned signal. The apparatus of this embodiment is characterized in that a signal-to-noise ratio can be improved by suitably selecting the modulation frequency of the signal.

Figure 7:
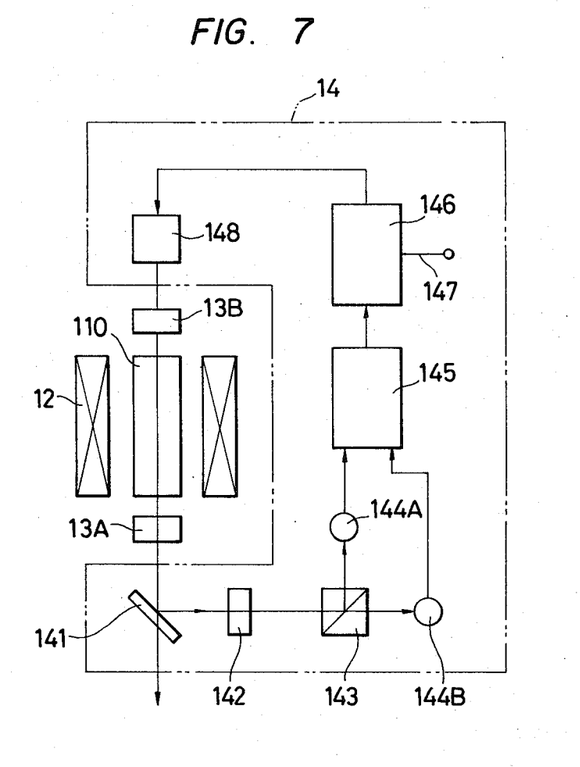
FIG. 7 is a block diagram showing the construction of still another embodiment of the apparatus for detecting the magneto-optical anisotropy of the present invention.

The Zeeman laser employed in the abovementioned embodiment is the heretofore known type in which the intensity of the right and left circularly polarized light is equal to each other and the composite wave becomes linearly polarized light. For this reason, the embodiment needs the elliptical polarizer as represented by 90A in FIG. 6. As an example to improve this point, an example of the Zeeman laser construction in which the laser light itself becomes elliptically polarized light is shown in FIG. 7. A magnetic field parallel to the optical axis is impressed upon a laser active substance 110 by means of a magnetic field generator 12. A light resonator is formed by two reflecting mirrors 13A and 13B. The output light of the Zeeman laser constructed in this manner becomes the right and left circularly polarized light having a varying frequency from each other as described already, but the intensity of the right and left circularly polarized light in the Zeeman laser used in the present invention is controlled in the following manner using a control system 14 encompassed by dotted lines in FIG. 7.

Namely, a part of the output light is separated by a beam splitter 141 and is passed through a quarter wavelength plate 142 whereby the right and left circularly polarized light becomes two rays of linearly polarized light that cross each other at a right angle. They are separated by a polarization analyzer 143 and their intensity are measured by light receivers 144A and 145B and compared by a comparator 145. If the difference, of the right and left circularly polarized light is not equal to a predetermined reference value applied from a reference value input terminal 147, deviation from the predetermined reference value is detected using a comparator 146 and a resonator length is adjusted using a driving mechanism 148 so that they become equal to each other. When the reference value is set to zero, the intensity of the right and left circularly polarized light becomes equal to each other and the composite wave becomes linearly polarized light as described already. When a reference value which is not zero is applied, there is obtained elliptically polarized light having elliptically in accordance with the reference value. In the elliptically polarized light thus obtained, the direction of its principal axis rotates with the time in the same way as the linearly polarized light shown in FIG. 6. Accordingly, it is possible to detect the change of the ellipticity using the same optical system as shown in FIG. 6.

That is to say, the elliptical polarization Zeeman laser shown in FIG. 7 is used as the light source 10 and the elliptical polarization generator 90A is removed because it is not necessary. According to this arrangement, the rays of light incident to the light receivers 34 and 35 are subjected to the intensity modulation and their amplitude corresponds to the ellipticity. Accordingly, the modulated amplitude of the ray of light incident to the light receiver 34 corresponds to the ellipticity of the light passing through the recording medium 20 and that of the light incident to the light receiver 35 corresponds to the ellipticity of the light emitted from the light source. For this reason, it is possible to detect the change of the ellipticity due to the optically anisotropic medium in the same way as in the embodiment shown in FIG. 3.

Figure 8:
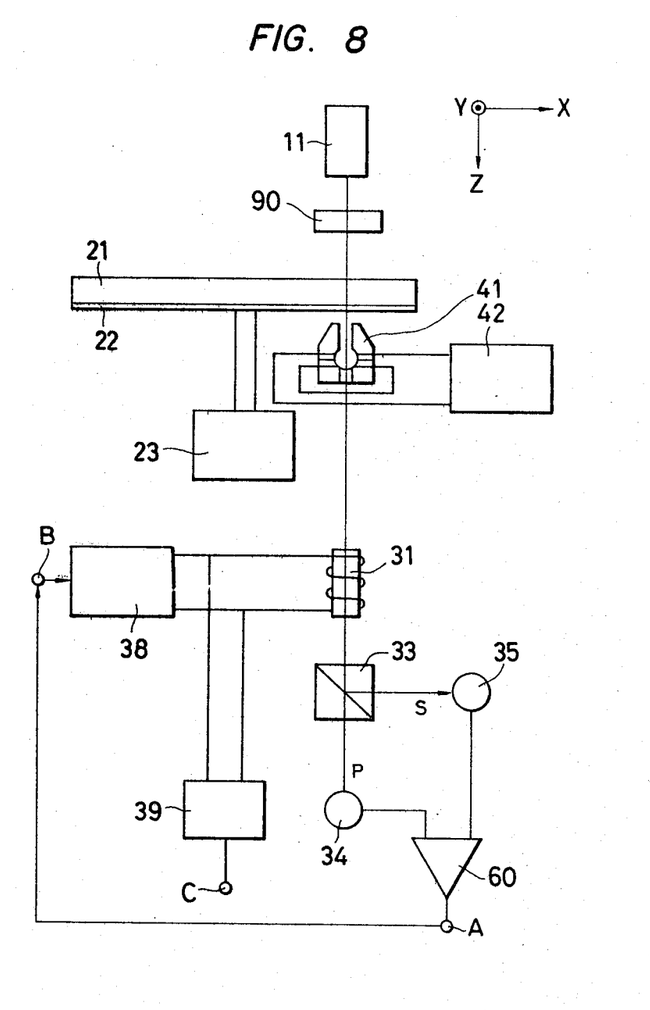
FIG. 8 is a block diagram showing the construction when the present invention is applied to an optical disc.

FIG. 8 shows still another embodiment of the present invention. This embodiment relates to an apparatus for recording and reproducing information on an optical disc using the magnetooptical anisotropy in the transverse magnetic field. The information disc is produced by forming the magnetic thin film 22 on the surface of the glass substrate 21 and is driven for rotation by the motor 23. A write magnetic head 41 is disposed close to the magnetic thin film 22 and is excited by a power source 42. The ray of light of the linearly polarized light laser 11 is converted into the circularly polarized light by a ¼-wavelength plate 90 and into the elliptically polarized light as it passes through the magnetic thin film 22, causes rotation in the orientation of the principal axis of the ellipticity polarized light as it further passes through a Faraday rotation element 31 and is then separated into two, mutually orthogonal, linearly polarized light by a polarization analyzer 33. Each polarized light component is incident to the light receiver 34, 35 and its intensity is compared with that of the other by a comparator 60 so that a signal corresponding to the difference of the intensity appears at the output terminal A. The Faraday rotation element 31 is excited by the power source 38 and its excitation current is measured by an excitation current meter 39. The measured value appears at the output terminal C. The signal appearing at the output terminal A of the comparator 60 is fed back to the input terminal B for controlling the excitation current of the power source 38. As magnetooptic recording media, various magnetic materials are known in the art. As the Faraday rotation element, there are also known various substances having light-transmitting property and a large Verdet constant.

Figure 9:
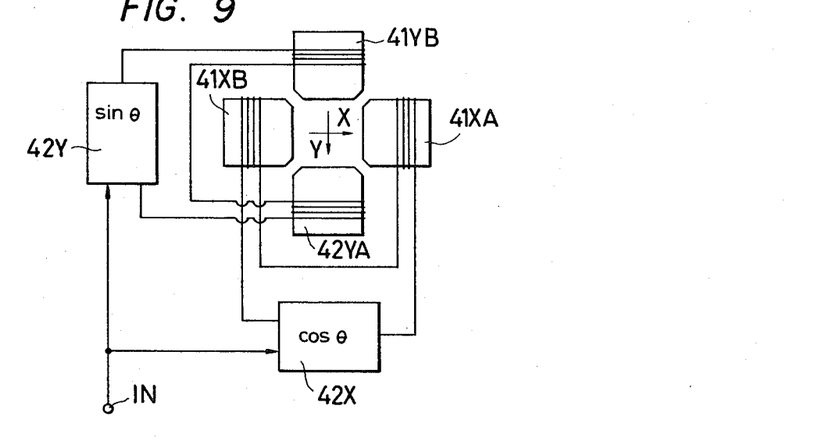
FIGS. 9 and 10(a)-(c) are schematic views useful for explaining the operation of the apparatus shown in FIG. 8.

Next, the principle of operation of the apparatus of the present invention will be explained. Initially, the method of writing information will be described. As viewed from the direction perpendicular to the disc surface, the magnetic head 41 consists of magnetic poles 41XA and 41XB for generating the magnetic field in the X direction and magnetic poles 41YA and 41YB for generating the magnetic field in the Y direction as shown in FIG. 9. These poles are excited by power sources 42X and 42Y, respectively. Within the disc surface, the magnetic thin film 22 is magnetized in an optional direction by regulating the ratio of the X direction excitation current and the Y direction excitation current. The size of the range to be magnetized is determined by the width of the gap of the magnetic head. Discrimination of the information, that is, 0 and 1 in the digital recording or a signal level in analog recording, is made by the azimuth of magnetization. In other words, if a rated input signal level impressed by the input terminal In is selected within the range of $-\pi/4 < \theta < \pi/4$, $\sin\theta$ and $\cos\theta$ are generated by a function generator, X-direction Y-direction magnetic fields are generated by excitation currents proportional to them, and the azimuth $\theta$ of the composite magnetic field relative to the X axis becomes equal to the input signal. Large quantities of information can be recorded by aligning minute magnetized regions while the disc is being rotated. As the recording method, the heretofore known thermo-magnetic recording methods (Curie point recording, compensation temperature recording, etc.) may be employed.

Next, a reproduction method of reading out the recorded information will be described. As shown in FIGS. 8 and 9, the X and Y axes are positioned within the surface of the optical disc while the Z axis is positioned perpendicularly to the surface, that is, in the direction of the optical path. The orientation of the polarization analyzer 33 is arranged in such a manner that the X direction linearly polarized light (p component) is incident to the light receiver 34 while the Y direction polarized light (s component) is incident to the light receiver 35.

Figure 10:
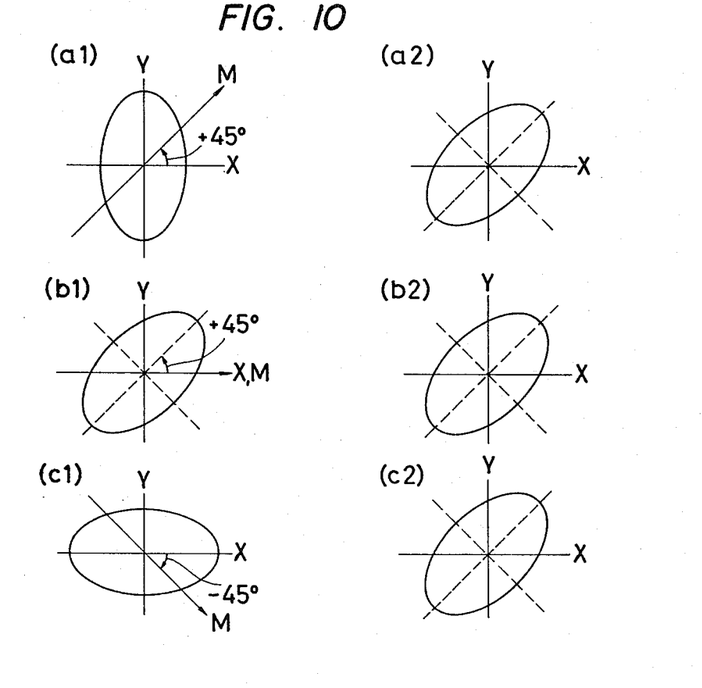

As the circularly polarized light generated by the light source 10 passes through the magnetic thin film 22, it is converted into the elliptically polarized light due to the magnetooptical effect (Voigt effect, in this case). As shown in FIG. 10(a1), if the magnetizing direction M is within the disc surface and is +45° relative to the X axis, the elliptically polarized light after the passage through the magnetic thin film is polarized in the orientation with the X- and Y-axes being the principal axes. Accordingly, the difference $\Delta I = I_X - I_Y$ between the intensity of the X direction polarization component $I_X$ and the intensity of the Y direction polarization component $I_Y$ scores the minimal value (negative value) in the case of the embodiment shown in this drawing. This difference signal appears at the output terminal A of FIG. 8, is applied to the control input terminal B of the power source 38, the control signal regulating the exciation current of the Faraday rotation element 31. As a result, as shown in FIG. 10(a2), the ray of light after the passage through the Faraday rotation element 31 has the azimuth of the principal axis of the elliptically polarized light rotated by −45° and stops rotating when $I_X$ and $I_Y$ become equal to each other.

To sum up the abovementioned, when the azimuth of the magnetization is inclined by +45° relative to the X axis as shown in FIG. 10(a1), the Faraday rotation angle is such an angle as to compensate for the inclination, that is to say, −45°, and the Faraday rotation element excitation current scores a large negative value.

Next, when the orientation of magnetization M coincides with the direction of the X axis as shown in FIG. 10(b1), the principle axis of the elliptically polarized light coming out from the magnetic thin film 22 is, as shown in FIG. 10(b2), inclined by 45° from the X axis. In consequence, the $I_X$ and $I_Y$ are equal to each other and the difference signal becomes zero. Hence, the Faraday rotation angle as well as the excitation current also become zero. Finally, as shown in FIG. 10(c1), when the direction of magnetization M is inclined by −45° from the X axis, the principal axis of the elliptically polarized light coincides with the X and Y axes, as shown in FIG. 10(c2), whereby the difference signal ΔI between $I_X$ and $I_Y$ scores a large positive value and the Faraday rotational angle compensating for the signal becomes +45° with the Faraday rotation element excitation current being a positive maximum value. In the intermediate state other than the abovementioned state, both Faraday rotation angle and excitation current score intermediate values, respectively.

The above may be summarized as follows. The orientation of the principal axis of the elliptically polarized light after passing through the magnetic thin film 22 depends upon the orientation of the magnetization M and its magnetization azimuth can be determined by the magnitude and polarity of the excitation current of the Faraday rotation element 31. Accordingly, in recording, if the orientation of the magnetization M is varied during recording in accordance with 0 and 1 of the input digital signal or with the height of the level of the input analog signal, the recorded content can be reproduced optically. In this case, the original signal can be reproduced as the magnitude and sign of the excitation current of the Faraday rotation element in accordance with the azimuth of the magnetization M. The reproduction signal is produced as output at the output terminal C via the measuring equipment 39 of the excitation current of the Faraday rotation element.

Figure 11:
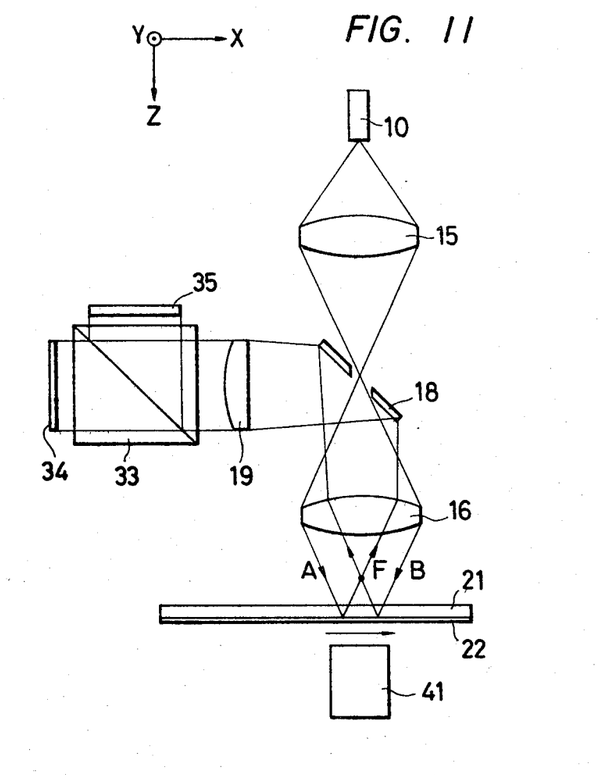
FIG. 11 is a block diagram showing the construction of still another embodiment of the apparatus for detecting the magneto-optical anisotropy of the present invention.
Figure 12:
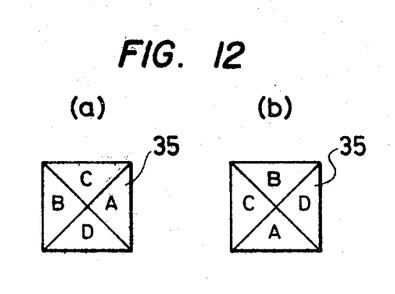
FIGS. 12(a) and 12(b) schematic views showing the principal portions forming the embodiment shown in FIG. 11.

FIG. 11 shows still another embodiment of the present invention. This embodiment is of the reflection type construction shown in FIG. 2. The ray of light from the light source 10 for the circularly polarized light or the elliptically polarized light is incident to the magnetic thin film 22 through a condenser lens 15, a reflecting mirror 18 having a hole and a focusing lens 16. The ray of light reflected on the surface of the thin film is focused at an image-forming point F and passes through the lens 16, the reflecting mirror 18, the lens 19 and the polarization analyzer 33 whereby the p component reaches the light receiver 34 while the s component reaches the light receiver 35. As viewed from such a direction that the rays of incident light to the light receivers 34 and 35 are also incident to the eyes of the observer, the light receivers 34 and 35 have a quartered construction such as shown in FIGS. 12(a) and 12(b) (with the divided ranges represented by A, B, C and D). As can be appreciated by tracing the rays of light, among the rays of light incident to the magnetic thin film 22, the p component of the ray of light A of which incident surface coincides with the sheet surface of the drawing reaches the light receiving element 34A while its s component reaches the light receiving element 35A. The p component of the ray of light B reaches the light receiving element 34B while its s component reaches the light receiving element 35B. Similarly, as to the rays of light whose incident surface is perpendicular to the sheet surface of the drawing, the ray of light incident from one side and reflected to the other side is incident to the light receiving elements 34C and 35C while the ray of light incident from the other side of the sheet surface and reflected to this side is incident to the light receiving elements 34D and 35D.

Figure 13:
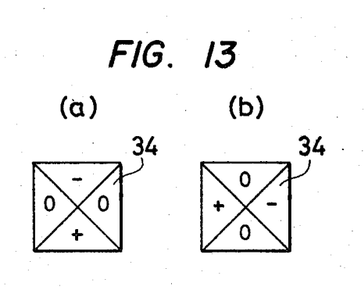
FIGS. 13(a) and 13(b) are schematic views useful for explaining the operation of the embodiment shown in FIG. 11.

It will be assumed here that the magnetic thin film 22 is magnetized by a magnetic head 41 in the direction parallel to the sheet surface (+x direction) as indicated by arrow, and that the incident, elliptically polarized light to the magnetic thin film 22 is elliptically polarized light of which x-direction polarization component parallel to the sheet surface is small and of which y component perpendicular to the sheet surface is by far greater than the x component. Under such a condition, there occur a longitudinal kerr effect to the rays of light A and B and a transverse effect to the rays of light whose incident surface is perpendicular to the sheet surface. As a result, the intensity of the ray of light incident to each light receiving element (p component for the light detection element 33) of the light receiver 34 changes in the following manner. That is to say, the intensity of the ray of light incident to each light receiving element is represented as shown in FIG. 13(a) with a reference set under a condition where the magnetization of the magnetic thin film 22 is zero. Thus, the light receiving ranges A, B, C and D of the light receiver 34 correspond to +, 1, 0 and 0, respectively, where + represents the increase, − does the decrease and 0 does no change or a slight change.

Under this state, when the magnetization of the magnetic thin film 22 inverses and faces in the negative direction of the x axis, the light intensity of each light receiving element inverses from + to − and vice versa with 0 remaining unaltered. In this manner, it is possible to identify by means of the intensity distribution pattern on the quartered light receiver whether the magnetization of the magnetic thin film faces in the positive direction of the x axis or in its negative direction. For some magnetic materials it may happen that the increase and decrease of the light intensity incident to the light receiving elements assume the opposite polarities to those mentioned above but there is no essential difference in the principle of identifying the magnetizing direction.

Next, consideration is made when the magnetic thin film 22 is magnetized in the direction perpendicular to the sheet surface of the drawing. In this case, the light intensity incident to each light receiving element changes as shown in FIG. 13(b). Namely, the light receiving ranges A, B, C and D of the light receiver 34 are 0, 0, + and −, respectively. When the magnetization inverses under this state, the abovementioned + and − inverse with each other.

To sum up, it is possible to record and reproduce four-value information on one minute spot. This four-value information corresponds to +x, −x, +y and −y depending on the orientation of the magnetization. Each of the magnetized states produces a varying intensity pattern on the quartered light receiver when reproduced optically. The technique described in this embodiment provides a high density recording/reproduction technique representing binary or non-binary information in accordance with the orientation of the magnetization. Incidentally, the light receiver 35 in this embodiment functions to provide a reference value of the light intensity in the same way as in the embodiment shown in FIG. 3.

Figure 14:
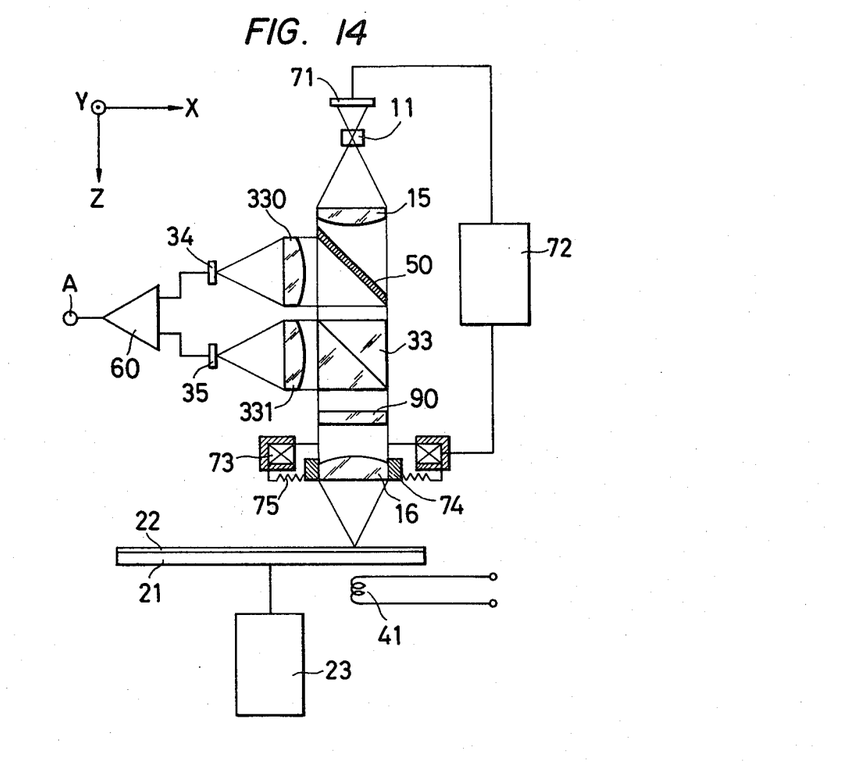
FIG. 14 is a block diagram showing the construction of still another embodiment of the apparatus for detecting the magneto-optical anisotropy of the present invention.

FIG. 14 shows still another embodiment of the present invention. The light source is a helium-neon laser or a semiconductor laser, for example. The state of polarization is linearly polarized light parallel to the sheet surface of the drawing, that is, the linearly polarized light in the x axis direction. This polarized light is hereinafter called "p polarized light". The ray of light from the light source 11 is made substantially parallel by a collimator lens 15 and passes through a beam splitter 50. This beam splitter is constructed by a transparent glass sheet, for example, and most of the p component pass through this splitter. Next, the laser light is incident to a polarizing prism 33. Most of the p component pass through this prism and are converted into the circularly polarized light or elliptically polarized light as they pass through a phase plate 90. The ray of the polarized light is then converged by a lens 16 and is then incident to a magnetic recording disc. The magnetic recording disc is produced by depositing the magnetic thin film 22 onto the surface of a glass or plastic substrate 21 and is driven for rotation by a motor 23. Recording of information is effected by locally magnetizing the magnetic thin film using a magnetic head 41. In this instance, 0 and 1 of the digital information can be distinguished whether the magnetizing direction, which is perpendicular to the disc surface, for example, faces the +z direction or the −z direction. In practice, however, it is desirable for realizing the high density that a recording area per bit information is as small as possible. Hence, it is more advisable to employ the thermomagnetic recording technique. In this technique laser beam is focused onto the disc surface which is more intense than in reproduction and the magnetized state is locally changed by heating a magnetic substance to a temperature higher than a certain critical point. This technique is well known in the art of the magneto-optic field.

Various substances are known for the magnetic thin film. A gadolinium-cobalt film formed by sputtering may be used, for example. This film is magnetized by the abovementioned method and the elliptically polarized light or the circularly polarized light is irradiated upon the film by the abovementioned method. The light reflected by the magnetic film passes again through the lens 16 and the phase plate 90 and is again incident to the polarizing prism 33. This re-incident light is in the polarized state different from the p component emitted from the laser, owing to the action of the phase plate 90 and to the magnetic Kerr effect on the magnetic film 22, that is to say, it is in the state of the elliptically polarized light. This light contains afresh an s component which is polarized in the direction perpendicular to the sheet surface of the drawing, that is, in the y direction. The p component and the s component are separated from each other by a polarization analyzer, or, the polarizing prism 33. The p component travels straight and its most parts return again to the laser 11. However, a part of the p component is separated by the beam splitter during its travel and is converged on the light receiver 34 by a lens 330. The s component separated by the polarizing prism 33 as the polarization analyzer is converged upon the light receiver 35 by a lens 331. The output electric signals of the light receivers 34 and 35 are applied to a differential amplifier 60 and its differential signal appears at the output terminal A.

The magnetic film 22 must be positioned in the proximity of the focal point of the laser light converged by the lens 16. Actually, however, the magnetic film 22 tends to deviate from the focal point due to the surface deviation arising from the rotation of the disc. If the film is out of the focal point, the light quantity of the p component from the reflection to its return to the laser and the light output of the laser varies in accordance with this change. This is a light feed-back effect. The light output of the laser is detected by detecting the light outgoing backwardly by means of a light receiver 71 and its output is fed to an electromagnet 73 via a feed-back amplifier 72.

On the other hand, an iron piece 74 is fixed to the focusing lens 16, both of lens and iron piece supported by a spring 75. According to this construction, when the position of the magnetic film 22 deviates from the focal point of the lens 16, the excitation current of the electromagnet 73 changes due to the abovementioned light feed-back effect so that the electromagnetic attraction to the iron piece 74 changes and the lens 16 is pulled back to the correct focal point. Automatic focal adjustment is made in this manner. The electromagnet 73 is arranged so as not to magnetize the magnetic film 22.

A so-called tracking technique, which prevents the focused spot of the laser light from coming out of the information recording track is well known in the art of the conventional optical disc technique.

Figure 15:
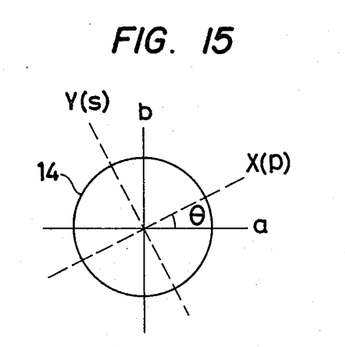
FIG. 15 is a schematic view showing the axis of polarization for explaining the operation of the embodiment shown in FIG. 14.

Next, the characteristic and arrangement of the phase plate as one of the constituent requirements of this embodiment will be described. This phase plate has two principal axes of polarization on the plane crossing at a right angle with each other on the plane pependicular to the optical path, that is to say, on the x-y plane of FIG. 14. The orientation of these two principal axes, or, the a axis and the b axis, are shown in FIG. 15. In other words, the x axis (p axis of the polarizing prism) and the y axis (s axis of the polarizing prism) are arranged so as to be inclined by an angle $\theta$ from the a axis and b axis, respectively. Further, it is assumed that there is a phase difference of a phase angle $2\Delta$ between the a axis and b axis. That is to say, when refractive indice in the directions of the a and b axes are $n_a$ and $n_b$, respectively, $2\pi(n_b-n_a)d/\lambda=2\Delta$, where d is a thickness of the phase plate and $\lambda$ is a wavelength. According to this arrangement, the light passing through the phase plate is converted into the elliptically polarized light (including the circularly polarized light).

Next, the reflection characteristic on the surface of the magnetized substance will be described. When reflection tensor representing the magnetic Kerr effect is $$\begin{pmatrix} R_p & K \\ K & R_s \end{pmatrix},$$

$R_p$ and $R_s$ represent the Fresnel reflection coefficients and K represents the Kerr reflection coefficient. If the imaginary part of K is $K^{(i)}$, the following equation represents the Kerr ellipticity:

$$E = K^{(i)}/R_p \tag{1}$$

Under the abovementioned condition, the intensity I of the light incident to the light receiver 35 is obtained in the following manner with the proviso that the optical axis of the incident light is perpendicular to the reflection surface.

$$I = I_r(S^2 - 2ES + A) \tag{2}$$

$$S = \sin 2\theta \cdot \sin 2\Delta \tag{3}$$

$$A = |K/R_P|^2 + C \tag{4}$$

In the abovementioned formulas, $I_r$ represents the Fresnel reflection light intensity, and A represents the ratio of the received light intensity to $I_r$ when $S=0$ or when $\theta=0$ or $\Delta=0$, and is a sum of the portion $|K/R_P|^2$ due to the Kerr effect and other portions C due to the stray light or to the incompleteness of the polarizing prism 33. Equivalently, the noises of the light receiver, dark current and electronic circuit are contained in C. When the magnetizing direction inverses, $K^{(i)}$ of the equation (1) or the sign of E inverses and the peak value of the signal output at that time is given as follows from the equation (2);

$$I_s = |I^{(+)} - I^{(-)}| = |4ESI_r| \tag{5}$$

Here, $I^{(\pm)}$ represents the received light intensity when the magnetization is in the positive or negative direction, respectively. The noise arising from the d.c. background is $$I_N = \eta(I^{(+)} + I^{(-)})/2 = \eta I_r(S^2 + A) \tag{6}$$

Here, $\eta$ represents fluctuation factor of light intensity received by the light receiver 35. In order for the signal to be detected, therefore, the following relation must at least be satisfied from equations (5) and (6);

$$4|ES| > \eta A$$

that is, $$|\sin 2\theta \cdot \sin 2\Delta| > \eta A/4|E| \tag{7}$$

As the effective value of the light intensity fluctuation factor, the ratio between the root mean square value of the fluctuation and the mean value of the light intensity may be used. Namely, in the embodiment shown in FIG. 14, equation (7) must be satisfied as one of the requirements when the phase plate of a phase difference $2\Delta$ is arranged at an azimuth $\theta$.

Next, the optimum points of $\Delta$ and $\theta$ can be obtained in the following manner from the condition which makes the signal-to-noise ration maximum;

$$S = \sin 2\theta \cdot \sin 2\Delta = \pm \sqrt{A} \tag{8}$$

However, the condition of the above equation is not necessarily essential. If the absolute value of S determined by this equation is extremely smaller in comparison with 1, the absolute value of S may be set to be greater than the optimum point given by the above equation. For, as can be appreciated from the equation (5), the absolute value of the signal output increases with an increasing value of $|S|$, and it is sometimes more advantageous practically to have a higher lever for the output signal even at the sacrifice of the signal-to-noise ratio to some extents.

To reduce the noise $I_N$, the light intensity fluctuation factor $\eta$ must be reduced, as can be understood from the equation (6). An effective method for this purpose will be described in the paragraph to follow. In FIG. 14, the p component light quantity incident to the light receiver 34 contains the noise component having the same phase as that of the signal of the light receiver 35. Accordingly, the noise contained in the signal appearing at the output terminal A can be reduced by making equal the mean values of signal intensity appearing at the two light receivers 34 and 35 through adjustment of the transmission factor of reflection factor of the optical system or through adjustment of gain of an electric signal system and obtaining the difference between them by use of a differential amplifier 60. In this manner, the light intensity fluctuation factor can effectively be reduced. Incidentally, the same effect can be obtained by connecting a light receiver 71 to the differential amplifier 60 instead of using the light receiver 34.

If $|S|$ becomes greater than the optimum point of equation (8), the signal-to-noise ratio decreases with $|S|$. In order for the signal to be detected, $|S|$ must satisfy the following equation (9);

$$|\sin 2\theta \cdot \sin 2\Delta| < 4|E|/\eta \tag{9}$$

Namely, the phase angle $2\Delta$ and aximuth $\theta$ of the phase plate must satisfy the condition of the formula (9). Since $|S| \leq 1$, however, the condition of the formula (9) can be satisfied automatically if the Kerr ellipticity $|E|$ is so great, or if the light quantity change ratio is so small, as to make the right side of equation (9) greater than 1.

As described above, in the optical system shown in FIG. 14, $|\sin 2\theta \cdot \sin 2\Delta|$ must fall within the range stipulated by equations (7) and (9) when the phase difference of the phase plate 90 is $2\Delta$ and the angle described by its principal axis with the polarizing direction of the incident linear polarized light (p polarized light) is $\theta$.

Figure 16:
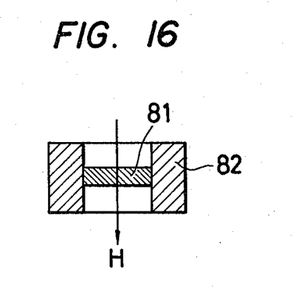
FIG. 16 is a schematic view showing another construction of the principal portions of the embodiment shown in FIG. 14.

In the embodiment shown in FIG. 14, a rotary polarization element (Faraday rotation element) may be employed in place of the phase plate 90. FIG. 16 shows an example of the construction of the rotary polarization element. This drawing is a sectional view of the rotary polarization element which is cut on the plane parallel to the sheet surface of FIG. 14. A magnetic field H is applied by a ring-like magnet 82 onto a disc 81 consisting of glass, rare eath, iron, garnet or the like. The direction of the magnetic field H is parallel to the optical path. The linearly polarized light passing through this disc has a polarizing direction which rotates with the optical axis as its axis. This angle, or the Faraday rotation angle $\phi$, varies with the magnetic field, the thickness of the disc 81 and the material of the disc.

When the rotary polarization element is employed, the condition which permits the detection of the signal is as follows. Namely, when the real part of the Kerr reflection factor K is defined as $K^{(r)}$ and the Kerr rotation angle, as $$G = K^{(r)}/R_p \tag{10}$$

the following conditions (11) and (12) must be satisfied simultaneously;

$$|\sin 4\phi| > \eta A/2|G| \tag{11}$$

$$|\tan 2\phi| < 2|G|/\eta \tag{12}$$

In comparison with the phase plate, the rotary polarization element is disadvantageous in the aspect of the weight of the magnet and in that magnetic shield must be considered so as not to allow the magnet 82 to act upon the magnetic film 22. Depending upon the material of the magnetic film 22 and upon the wavelength of the laser, however, it sometimes happens that the Kerr ellipticity E is small whereas the Kerr rotational angle G is large. In such a case, the rotary polarization element must be used.

The present invention can be applied to the observation of magnetic domains and to the detection of magnetic bubbles.

In the foregoing embodiments, the change in the ellipticity arising from the optical elements other than the optically anisotropic medium as the object for the measurement can be compensated for by adjusting the ellipticity generated by the elliptically polarized light generation means.

INDUSTRIAL APPLICABILITY

The present invention can be applied to the magneto-optic memory in which information is recorded in accordance with the state of magnetization of a magneto-optical medium, and the recorded information is optically reproduced.

What is claimed is:

1. The apparatus for detecting magneto-optical anisotropy consisting of a light source, a magneto-optically anisotropic medium to which the ray of light from said light source is irradiated, a polarization analyzer to which the ray of light from said medium is incident and a light detector to which the ray of light obtained via said polarization analyzer is incident, the improvement wherein said apparatus is equipped with means for generating ellipticaly polarized light on an optical path consisting of said light source, said magneto-optically anisotropic medium, said polarization analyzer and said light detector, and said means for generating the elliptically polarized light are arranged in such a manner that the ray of light travelling towards said polarization analyzer remains the elliptically polarized light when it is incident to said polarization analyzer, wherein the ray of light emitted by said light source is linearly polarized light, and said means for generating the elliptically polarized light is a phase plate with the phase difference $2\Delta$ and with the principal axis oriented at an angle $\theta$ with respect to the polarization direction of said linearly polarized light, which is characterized by that the quantity $|\sin 2\theta \cdot \sin 2\Delta|$ is stipulated within the range given by the following formula:

$$\eta A/4E < |\sin 2\theta \cdot \sin 2\Delta| < 4|E|/\eta,$$

where E is the Kerr ellipticity on a magnetized reflecting surface, A is the ratio of the received light intensity to the intensity of the Fresnel reflection light under the condition of $\Delta = 0$ or $\theta = 0$, and $\eta$ is the fluctuation factor of the received light intensity.

* * * * *